United States Patent
Bolz et al.

(10) Patent No.: US 10,420,924 B2
(45) Date of Patent: Sep. 24, 2019

(54) CONNECTOR DEVICE FOR A FLUID SYSTEM FOR MEDICAL PURPOSES

(71) Applicant: B. Braun Melsungen AG, Melsungen (DE)

(72) Inventors: Johannes Bolz, Kassel (DE); Jens Jörn, Kassel (DE); Andreas Katerkamp, Melsungen (DE)

(73) Assignee: B. Braun Melsungen AG (DE)

( * ) Notice: Subject to any disclaimer, the term of this patent is extended or adjusted under 35 U.S.C. 154(b) by 834 days.

(21) Appl. No.: 14/868,108

(22) Filed: Sep. 28, 2015

(65) Prior Publication Data

US 2016/0089529 A1    Mar. 31, 2016

(30) Foreign Application Priority Data

Sep. 30, 2014  (DE) .................. 10 2014 219 814

(51) Int. Cl.
*A61M 39/10*     (2006.01)
*F16L 41/02*     (2006.01)
(Continued)

(52) U.S. Cl.
CPC ........ *A61M 39/10* (2013.01); *A61M 39/1011* (2013.01); *A61M 39/26* (2013.01);
(Continued)

(58) Field of Classification Search
CPC .. A61M 39/10; A61M 39/26; A61M 39/1011; F16L 29/02; F16L 13/103; F16L 41/023; F16L 13/0209
See application file for complete search history.

(56) References Cited

U.S. PATENT DOCUMENTS

| | | |
|---|---|---|
| 3,797,486 A | 3/1974 | Shaps |
| 4,911,705 A | 3/1990 | Heinzerling et al. |

(Continued)

FOREIGN PATENT DOCUMENTS

| | | |
|---|---|---|
| DE | 10 2007 020 859 A1 | 11/2008 |
| DE | 10 2008 034 919 A1 | 5/2009 |

(Continued)

OTHER PUBLICATIONS

The European Search Report for the related European Patent Application No. 15184194.7 dated Feb. 4, 2016.

*Primary Examiner* — James M Hewitt, II
(74) *Attorney, Agent, or Firm* — RatnerPrestia

(57) ABSTRACT

A connector device for a fluid system for medical purposes is disclosed that includes a main housing having a fluid flow chamber forming two channel portions leading in different directions towards two open attachments, wherein the attachments are provided for connection to a fluid line or a fluid reservoir, and with an attachment port which opens into the fluid flow chamber and which has a closure arrangement and which includes a Luer connecting portion. The fluid flow chamber has a dimensionally stable flow-guiding wall which is arranged between the two channel portions in the fluid flow chamber and protrudes freely with a front edge towards the attachment port in such a way that the closure arrangement, upon opening of the closure arrangement, interacts with the front edge of the flow-guiding wall in order to effect flow of fluid out of the attachment port into only one channel portion.

12 Claims, 1 Drawing Sheet

(51) Int. Cl.
*A61M 39/26* (2006.01)
*F16L 13/02* (2006.01)
*F16L 13/10* (2006.01)
*F16L 29/02* (2006.01)

(52) U.S. Cl.
CPC ......... *F16L 13/0209* (2013.01); *F16L 13/103* (2013.01); *F16L 29/02* (2013.01); *F16L 41/023* (2013.01); *A61M 2039/1027* (2013.01); *A61M 2039/1083* (2013.01); *A61M 2039/1088* (2013.01)

(56) References Cited

U.S. PATENT DOCUMENTS

| | | |
|---|---|---|
| 5,098,405 A | 3/1992 | Peterson et al. |
| 5,147,333 A | 9/1992 | Raines |
| 5,335,686 A * | 8/1994 | Isringhausen ......... F16L 41/023 137/14 |
| 5,632,300 A * | 5/1997 | Isringhausen ......... F16L 41/023 137/269 |
| 5,810,768 A | 9/1998 | Lopez |
| 6,569,117 B1 | 5/2003 | Ziv et al. |
| 7,165,571 B1 * | 1/2007 | Buzdum ................. F16L 41/02 137/112 |
| 7,931,627 B2 | 4/2011 | Fangrow, Jr. |
| 2005/0134038 A1 * | 6/2005 | Walsh ................... F16L 41/021 285/125.1 |
| 2007/0145743 A1 * | 6/2007 | Greenberger ......... F16L 37/092 285/322 |
| 2009/0124983 A1 | 5/2009 | Ferrari |

FOREIGN PATENT DOCUMENTS

| | | | |
|---|---|---|---|
| EP | 2 810 685 A1 | 12/2014 | |
| GB | 576406 A * | 4/1946 | ........... F16L 41/023 |
| WO | 96/40359 A1 | 12/1996 | |
| WO | 2008/043069 A2 | 4/2008 | |
| WO | 2008/135475 A1 | 11/2008 | |
| WO | WO-2013032714 A2 * | 3/2013 | .......... A61M 39/223 |

* cited by examiner

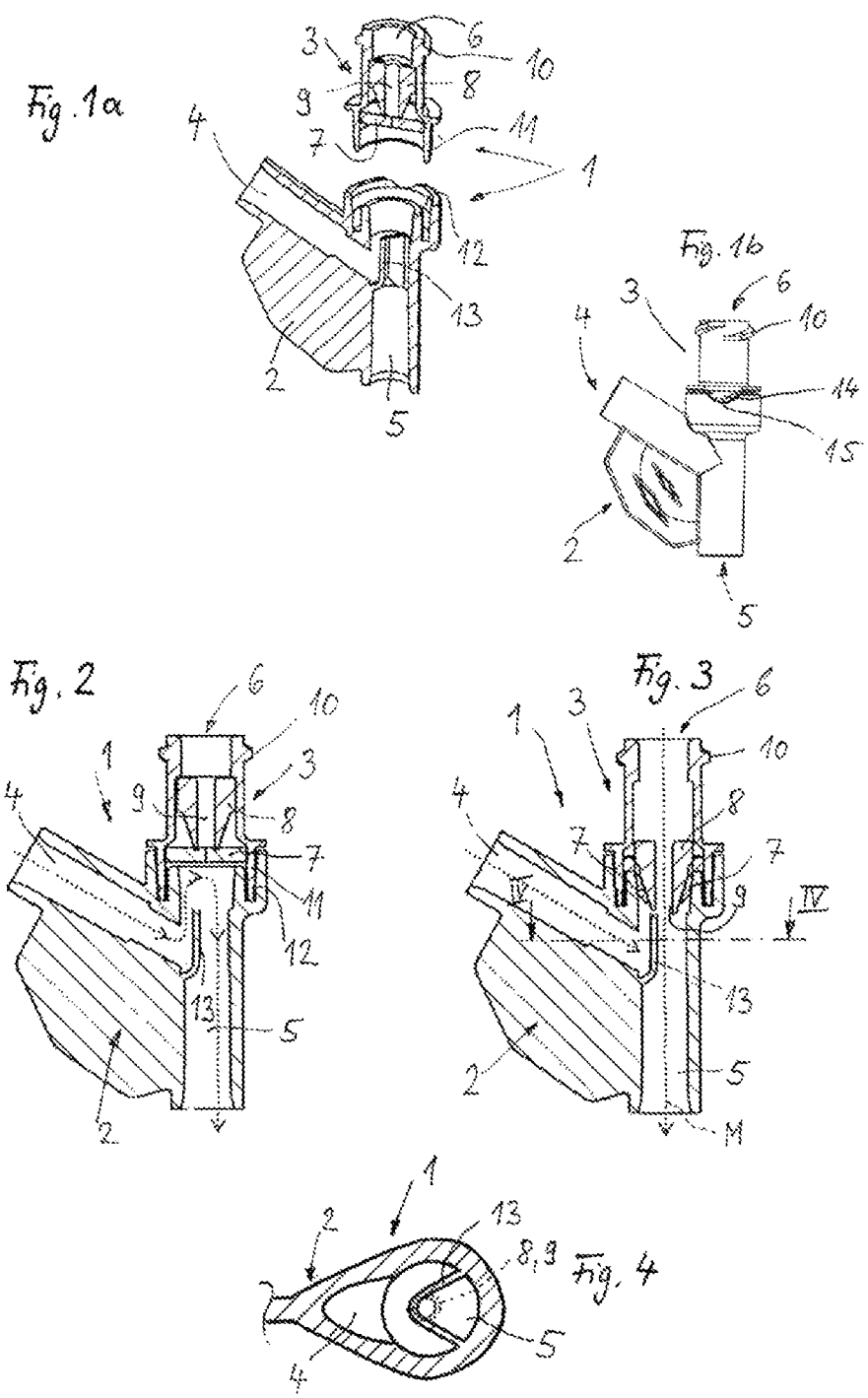

CONNECTOR DEVICE FOR A FLUID SYSTEM FOR MEDICAL PURPOSES

CROSS-REFERENCE TO RELATED APPLICATIONS

This application claims priority from German Patent Application No. 10 2014 219 814.3, filed on Sep. 30, 2014, the disclosure of which is hereby incorporated by reference in its entirety into this application.

FIELD OF THE DISCLOSED SUBJECT MATTER

The disclosed embodiments relate to a connector device for a fluid system for medical purposes, with a main housing which has a fluid flow chamber that forms channel portions leading in different directions towards two open attachments, wherein the attachments are provided for connection to in each case a fluid line or a fluid reservoir, and also with an attachment port which opens into the fluid flow chamber and is provided with a closure arrangement and which comprises a connecting portion for connection to an attachment part.

BACKGROUND

A related connector device is known from U.S. Pat. No. 7,931,627 B2. The related connector device is provided as a Y port for a medical infusion system. A fluid flow chamber, which forms several channel portions, is arranged in a main housing. Two channel portions branch in two different directions towards a respective open attachment, which can be connected in each case to a hose line that leads to a catheter or to a fluid reservoir receptacle. Moreover, the main housing has an attachment port which, in a continuation of one channel portion, opens in an opposite direction and comprises a Luer connecting portion in order to be able to attach a corresponding Luer attachment part such as a syringe or a fluid reservoir receptacle. A flexible check valve is provided in the fluid flow chamber and is able to close one channel portion at the branch to the other channel portion inside the fluid flow chamber. The flexible, tab-like valve does not completely shut off this channel portion, and instead it merely reduces the flow through the channel portion.

SUMMARY

An aspect of the disclosed subject matter is to make available a connector device, of the type mentioned at the outset, which is of a simpler design and permits safe, low-contamination handling.

This aspect is achieved by the fact that the fluid flow chamber has a dimensionally stable flow-guiding wall which is rigidly arranged between the two channel portions in the fluid flow chamber and protrudes freely with a front edge towards the attachment port in such a way that the closure arrangement, in an open position, interacts with the front edge of the flow-guiding wall in order to obtain a flow of fluid from the attachment port at least substantially to only one channel portion. According to the disclosed subject matter, the flow of fluid from the attachment port is focused on the one channel portion by means of the opening closure arrangement interacting with a partial portion of the flow-guiding wall. Preferably, the closure arrangement is formed by an elastically flexible closure membrane in conjunction with a movable actuating body, which is arranged to be linearly movable in order to open the closure membrane. The flow-guiding wall is arranged rigidly in the fluid flow chamber and, with the closure membrane closed, permits a corresponding flow of fluid between one and the other channel portion and, if appropriate, deflects the flow. The dimensionally stable flow-guiding wall permits a defined and constant flow of fluid through the fluid flow chamber, as long as the closure arrangement shuts off the attachment port. Therefore, according to the disclosed subject matter, a separate check valve or a clamp in a fluid line for the attachment of the one channel portion is not needed. The solution according to the disclosed subject matter is suitable in a particularly advantageous manner for a Y port within a medical infusion or transfusion system, wherein preferably an attachment of one channel portion continues into a patient line to a catheter, and the attachment of the other channel portion leads to a fluid reservoir receptacle, in which a medical infusion solution is stored that is delivered to the patient via the Y port and the patient line. The attachment port of the connector device thus used preferably serves, depending on the needs of the patient, to additionally deliver highly effective medicaments containing high-dose medical active substances. A suitable attachment part can be an infusion syringe provided with a Luer lock or a Luer slip connecting portion, which can be easily connected by hand to the corresponding connecting portion of the attachment port and released again. In doing so, the closure arrangement is forcibly opened and then closed again. Alternatively, the connecting portion for enteral applications is designed as an enteral small bore connector, which forms an enteral connecting portion that is incompatible with non-enteral attachment portions. This ensures that enteral functional parts cannot be connected to non-enteral functional parts.

Advantageously, the attachment port is oriented coaxially and flush with the channel portion of the main housing into which the fluid delivered through the attachment port is intended to be conveyed. By contrast, the other channel portion is preferably oriented in the manner of a Y branch at an angle to the first channel portion in the main housing. The attachments of the main housing, into which the two channel portions open outwards, can be provided with suitable connectors in order to make it easier to fit a corresponding hose line or an attachment nozzle of a fluid reservoir receptacle or of another connection part. In its open position, the movable actuating body can be positioned just above a front edge of the flow-guiding wall serving as partial portion or it can also be positioned bearing on the front edge. Alternatively, in the open position, the movable actuating body or the flexible closure membrane can nestle laterally on a corresponding partial portion of the flow-guiding wall, such that the flow of fluid delivered through the attachment port is thereby conveyed onwards into the channel portion that is flush with the attachment port.

In one embodiment of the disclosed subject matter, the flow-guiding wall is integrated in one piece in the main housing. The flow-guiding wall is preferably formed in one piece from a suitable plastics material during the production of the main housing.

In a further embodiment of the disclosed subject matter, the flow-guiding wall, at the free front edge, has an arc-shaped or V-shaped curvature in cross section over a partial area coaxial to a central longitudinal axis of the attachment port, wherein the flow-guiding wall is formed in a mouth region where one channel portion leads into the other channel portion. The free front edge comes into contact at least in part with the closure arrangement as soon as the closure arrangement is opened and is deformed/shifted in the direction of the fluid flow chamber. Accordingly, the flow-guiding wall forms a groove which extends coaxially or axially parallel to the channel portion in which the fluid delivered through the Luer attachment part is intended to be conveyed.

In a further embodiment of the disclosed subject matter, as part of the closure arrangement, a movable actuating body for opening a flexible closure membrane in accordance with a connection to a Luer attachment part is mounted in the attachment port. This ensures that the closure membrane reliably opens when a Luer attachment part is attached to the attachment port. The closure membrane is produced from an elastically flexible plastics material, in particular silicone, and slit, such that it opens upon elastic deformation. Moreover, the actuating body is provided with a through-channel which, on account of its cross section of flow, ensures a safe and constant delivery of a medical fluid from the Luer attachment part into the fluid flow chamber.

In a further embodiment of the disclosed subject matter, the flow-guiding wall protrudes in the direction of the attachment port in such a way that the actuating body and/or the flexible closure membrane, in the open position of the closure arrangement, is in contact with partial areas of the flow-guiding wall in such a way that a flow of fluid delivered into the attachment port from the Luer attachment part flows at least substantially into the channel portion. Corresponding wall portions or surface portions of the actuating body or of the closure membrane can be in contact with corresponding partial areas of the flow-guiding wall in the open position. Corresponding partial areas of the flow-guiding wall are front wall areas or lateral wall areas, such that the actuating body and/or the flexible closure membrane can, in the open position, be positioned at the front of the flow-guiding wall or laterally next to the flow-guiding wall.

In a further embodiment of the disclosed subject matter, the actuating body and/or the flexible closure membrane, in the open position of the closure arrangement, are positioned on or next to at least a partial area of the flow-guiding wall. Positioning is to be understood as meaning that the actuating body and/or the flexible closure membrane are arranged either at a short distance on or next to the corresponding partial area of the flow-guiding wall or in suitable contact on or next to the partial area of the flow-guiding wall.

In a further embodiment of the disclosed subject matter, a curvature of the free front edge is adapted to a through-channel of the actuating body, coaxial to the central longitudinal axis of the attachment port, in such a way that a groove thereby formed in the flow-guiding wall, on a side facing towards one channel portion, is flush with the through-channel of the actuating body when the actuating body is moved to its open position. The front face of the actuating body directed towards the front edge of the flow-guiding wall can bear on said front edge or can be positioned at a short distance from it when the actuating body is shifted to the open position. The connection between the through-channel and the other channel portion thus remains open in order to permit the desired injection of a medicament through the attachment port to the channel portion and thus in particular to the patient line.

In a further embodiment of the disclosed subject matter, the flow-guiding wall is designed for one channel portion as a flow-guiding surface which deflects a stream of fluid and which causes a deflection, in the direction of the attachment port, of fluid flowing out of one channel portion in the direction of the other channel portion. With the closure arrangement closed, the flow-guiding surface formed by the flow-guiding wall permits a defined and constant flow deflection of the corresponding medical fluid. The cross sections of flow in the area of one channel portion, in the area of the other channel portion and in the area of the deflection by the flow-guiding wall are preferably identical in terms of their flow surface area, such that a constant stream of fluid can flow through the fluid system.

Aspects of the disclosed subject matter are also achieved by the fact that the attachment port is provided in a housing component which is produced separately from the main housing and which is produced from a more inert plastics material than a plastics material of the main housing, in order to achieve greater chemical resistance than the main housing, in particular greater resistance to high-dose medical active substances that can be delivered at the attachment port to the fluid system. This avoids a contamination of the attachment port and, in particular, a reaction of the plastics material of the attachment port with correspondingly delivered toxic medical active substances, such that the attachment port can be reliably used to add several different types of medical active substances to the fluid system and, in particular, to a patient line. According to the disclosed subject matter, suitable inert materials for the housing component are, in particular, polyethylene (PE), polypropylene (PP), polysulphone (PSE) or copolyester. Suitable plastics for the main housing are polycarbonate (PC) or acrylonitrile butadiene styrene (ABS).

In a further embodiment of the disclosed subject matter, the housing component having the attachment port is connected tightly to the main housing by cohesive bonding, in particular by gluing or welding. Particularly advantageously, an adhesive that can be set by UV radiation is used for the gluing.

Further advantages and features of the disclosed subject matter will become clear from the claims and from the following description of exemplary embodiments of the disclosed subject matter, with reference to the drawings.

BRIEF DESCRIPTION OF THE DRAWINGS

FIG. 1a shows a sectional and perspective exploded view of an embodiment of a connector device according to the disclosed subject matter in the form of a Y port, FIG. 1b shows the connector device according to FIG. 1a in a side view, FIG. 2 shows a longitudinal section through the connector device according to FIG. 1 in a closed position of a flexible closure membrane, FIG. 3 shows the connector device according to FIG. 2 in an open position of the flexible closure membrane, and FIG. 4 shows, in an enlarged cross-sectional view, a section through the connector device according to FIGS. 1 to 3 along the section line IV-IV in FIG. 3.

DETAILED DESCRIPTION

A connector device according to FIGS. 1 to 4 is provided for use in an intravenous infusion system for medical purposes. The connector device 1 is designed as a so-called Y port which makes available a total of three attachments, described in more detail below, which combine within the connector device 1 to form a fluid flow chamber comprising channel portions 4, 5 that branch in the shape of a Y. The fluid flow chamber formed by the channel portions 4, 5 is arranged within a main housing 2, which is produced in one piece from plastic. The first channel portion 4, extending obliquely upwards to the left in FIGS. 1 to 3, has, at its outer front end area, an attachment for connecting the main housing 2 to a fluid reservoir, in particular a bottle or a bag that stores a suitable medical infusion solution. The channel portion 5 pointing downwards in FIGS. 1 to 3 has, in the area of its lower front end, an attachment for connection to a hose line serving as a patient line, which hose line leads to a catheter that can be delivered intravenously to the patient.

To be able in particular to supply the patient with additional medicaments, in particular in the form of high-dose medical active substances, the connector device 1 additionally has an attachment port 6 which, in the views according to FIGS. 1 to 3, is arranged on top of the main housing 2 in a coaxial continuation of the channel portion 5. The attachment port 6 is formed by a separate plastics component 3, which is made of a plastic that is more inert than the plastics material of the main housing 2. Accordingly, the separately produced plastics component 3 has greater chemical resistance to medical active substances that are delivered through the attachment port 6 of the connector device 1 and from there to the patient line.

The housing component 3 is designed as a rotationally symmetrical hollow-body component which is essentially coaxial to a central longitudinal axis M of the channel portion 5 and which is open both towards the outside, i.e. at the top, and also inwards to the fluid flow chamber. The housing component 3 forms the attachment port 6 which, on its outer jacket in the area of an upper front end, is provided with a Luer lock connecting portion 10 in order to permit the attachment of a Luer lock attachment part, such as, in particular, a syringe provided with a Luer lock connector. An elastically flexible closure membrane 7, preferably made of silicone, is arranged in the attachment port 6. In the unstressed state, the closure membrane 7 tightly closes off the attachment port 6, both towards the fluid flow chamber and also towards the outside. The closure membrane 7 is slit, such that it can open inwards into the fluid flow chamber in the event of elastic deformation. The closure membrane 7 is clamped between the housing component 3 and a front flange of the main housing 2, which flange delimits the channel portion 5 at the top. Arranged coaxially around the front flange, an annular receiving groove 12 is provided in the main housing 2, into which annular receiving groove 12 a cylindrical plug-in flange 11 of the housing component 3 can be inserted free of play. In this inserted state, the tight connection and fixing of the housing component 3 relative to the main housing 2 is obtained by cohesive bonding, in the present case by gluing with a liquid adhesive that can be set by UV radiation. Profiles 14, 15, which are provided on the circumference of the housing component 3 and of the main housing 2 and complement each other, prevent rotation and permit positionally precise orientation of the housing component 3 relative to the main housing 2.

On an outer face of the closure membrane 7 directed towards the front opening of the attachment port 6, the closure membrane 7 is assigned a piston-like actuating body 8, which is mounted displaceably in the attachment port 6 coaxially with respect to the central longitudinal axis M. The actuating body 8 has a through-channel 9 which is coaxial to the central longitudinal axis M and which is open at both ends of the actuating body 8.

The actuating body 8 is also produced from a suitable plastics material. Preferably, the plastics material of the actuating body 8 also has a high degree of chemical resistance to high-dose medical active substances that are delivered through the attachment port 6 of the connector device 1.

In the fluid flow chamber of the connector device 1, in a region where the first channel portion 4 opens into the second channel portion 5, a flow-guiding wall 13 is provided, which is dimensionally stable and is formed in one piece from the plastics material of the main housing 2 in the fluid flow chamber. As can be clearly seen from FIGS. 1 and 4, the flow-guiding wall 13, seen in a plan view, has a V-like orientation in the channel portion 5, wherein the flow-guiding wall 13 has a wall curved in an arc shape or V shape in cross section, as seen in the plan view (FIG. 4) according to the section line IV-IV in FIG. 3, which wall merges into the inner wall of the channel portion 5 in the area of an inner wall half lying opposite the mouth portion of the channel portion 4. In this way, on the side directed away from the mouth portion of the channel portion 4, the flow-guiding wall 13 forms a groove which extends coaxially or axially parallel with respect to the central longitudinal axis M. The corresponding wall of the flow-guiding wall 13 terminates flush and tight with the inner wall of the channel portion 5 on opposite sides over the entire height of the wall portion extending parallel to the inner wall of the channel portion 5. At a lower end area of the flow-guiding wall 13, relative to the vertical orientation in the view according to FIGS. 2 and 3, the flow-guiding wall 13 has a trough-like curvature which extends to the remaining, opposite inner wall portion of the channel portion 5 and merges there into the inner wall portion of the channel portion 5 below the mouth area of the channel portion 4. The trough portion thus formed accordingly extends in the shape of a portion of a ring underneath the vertically oriented and parallel V-shaped wall portions of the flow-guiding wall 13 and forms a catching basin for fluid flowing from the first channel portion 4 into the fluid flow chamber, as is indicated by the dotted arrows in FIGS. 2 and 3. Accordingly, for the flow of fluid guided through the first channel portion 4, the flow-guiding wall 13 forms a deflection surface, by means of which the flow of fluid in the mouth area leading to the channel portion 5 is backed up by the flow-guiding wall 13 and deflected in the direction of the closure membrane 7. With the closure membrane 7 closed, the fluid flows over the upper front edge area of the flow-guiding wall 13 serving as partial area and is deflected downwards into the second channel portion 5 (FIG. 2). It is thus ensured that no dead water region arises in the fluid flow chamber.

As soon as the actuating body 8 is moved downwards in the direction of the channel portion 5, as a result of a syringe connected to a Luer connector being mounted on the attachment port 6, the flexible closure membrane 7 is forced to open. The actuating body 8 can be moved downwards until its lower end face, directed towards the channel portion 5 and surrounding the through-channel 9, comes to bear on the upper front edge area of the flow-guiding wall 13 or remains at a distance directly above this front edge area. It will be seen from FIG. 4 that the orientation and arrangement of the curvature of the flow-guiding wall 13, seen in cross section, is adapted to the actuating body 8 such that the lower front surface area of the actuating body 8, which surface area surrounds the through-channel 9, is positioned flush with and above the front edge area of the flow-guiding wall 13 as soon as it is moved to its open position. In this way, an inner wall of the through-channel 9 of the actuating body 8 lies, coaxially with respect to the central longitudinal axis M, flush with a wall side of the flow-guiding wall 13 directed towards the channel portion 5. The flow of fluid indicated by the dotted arrow along the central longitudinal axis M in FIG. 3, namely of fluid that is delivered from the syringe through the attachment port 6 of the connector device 1, therefore flows through the through-channel 9, along the flow-guiding wall 13 in the area of the channel portion 5, and to the lower attachment of the channel portion 5. Since the lower front edge area of the actuating body 8 is at least essentially flush with the upper front edge area of the flow-guiding wall 13, the flow of fluid delivered through the attachment port 6 via the syringe does not, aside from negligible amounts of fluid, pass into the first channel portion 4, such that an undesired upward flow of this fluid delivered via the attachment port 6 is avoided. Quantities of fluid that move in the direction of the channel portion 4 encounter the fluid of the channel portion 4, and the water column created by said fluid, such that the return flow into this channel portion 4 is negligible from the medical point of view.

As soon as the corresponding Luer attachment part, in the present case the syringe, is removed again from the attachment port 6, the actuating body 8 necessarily returns to its rest position according to FIG. 2, and the closure membrane 7 likewise recovers its leaktight and closed starting position according to FIG. 2.

In exemplary embodiments of the disclosed subject matter that have not been shown, the flow-guiding wall 13 and the actuating body 8 and/or the flexible closure membrane 7 are adapted to one another in such a way that, in the open position of the closure arrangement, the actuating body 8 or the flexible closure membrane 7 engages in part in the groove area formed by the flow-guiding wall 13, such that the actuating body and/or the flexible closure membrane are positioned next to the flow-guiding wall 13. For this purpose, a front edge area of the flow-guiding wall 13 and a front surface area of the actuating body are mutually radially offset with respect to the central longitudinal axis M. In this way, the conically tapering area of the actuating body 8 can engage partially in the groove area.

The invention claimed is:

1. A connector device for a fluid system for medical purposes, comprising:
   a main housing which has a fluid flow chamber that forms channel portions leading in different directions towards two open attachments,
   wherein the attachments are provided for connection to in each case a fluid line or a fluid reservoir, and also with an attachment port which opens into the fluid flow chamber and is provided with a closure arrangement and which comprises a connecting portion for connection to an attachment part,
   wherein the fluid flow chamber has a dimensionally stable flow-guiding wall which is rigidly arranged between the two channel portions in the fluid flow chamber and protrudes freely with a front edge towards the attachment port in such a way that the closure arrangement, in an open position, interacts with the front edge of the flow-guiding wall in order to obtain a flow of fluid from the attachment port at least substantially to only one channel portion,
   wherein the closure arrangement includes a movable actuating body that is mounted in the attachment port.

2. The connector device according to claim 1, wherein the connecting portion is designed as a Luer slip or Luer lock connecting portion.

3. The connector device according to claim 1, wherein the connecting portion is designed as an enteral small bore connector.

4. The connector device according to claim 1, wherein the flow-guiding wall is integrated in one piece in the main housing.

5. The connector device according to claim 1, wherein the flow-guiding wall, at the free front edge, has an arc-shaped or V-shaped curvature in cross section over a partial area coaxial to a central longitudinal axis (M) of the attachment port, and wherein the flow-guiding wall is formed in a mouth region where one channel portion leads into the other channel portion.

6. The connector device according to claim 1, wherein, as part of the closure arrangement, the movable actuating body is configured to open a flexible closure membrane in accordance with a connection to a Luer attachment part.

7. The connector device according to claim 6, wherein the flow-guiding wall protrudes in the direction of the attachment port in such a way that the actuating body and/or the flexible closure membrane, in the open position of the closure arrangement, are in contact with partial areas of the flow-guiding wall in such a way that a flow of fluid delivered into the attachment port from the Luer attachment part flows at least substantially into the channel portion.

8. The connector device according to claim 7, wherein the actuating body and/or the flexible closure membrane, in the open position of the closure arrangement, are positioned on or next to at least a partial area of the flow-guiding wall.

9. The connector device according to claim 6, wherein a curvature of the free front edge of the flow-guiding wall is adapted to a through-channel of the actuating body, coaxial to the central longitudinal axis (M) of the attachment port, in such a way that a groove thereby formed in the flow-guiding wall, on a side facing towards one channel portion, is flush with the through-channel of the actuating body when the actuating body is moved to its open position.

10. The connector device according to claim 1, wherein the flow-guiding wall is designed for one channel portion as a flow-guiding surface which deflects a stream of fluid and which causes a deflection, in the direction of the attachment port, of fluid flowing out of one channel portion in the direction of the other channel portion.

11. The connector device according to claim 1, wherein the attachment port is provided in a housing component which is produced separately from the main housing and which is produced from a more inert plastics material than a plastics material of the main housing, in order to achieve greater chemical resistance than the main housing to medical active substances that can be delivered at the attachment port to the fluid system.

12. The connector device according to claim 11, wherein the housing component having the attachment port is connected tightly to the main housing by cohesive bonding, in particular by one of gluing or welding.

* * * * *